United States Patent [19]

Marquis et al.

[11] Patent Number: 4,626,596

[45] Date of Patent: Dec. 2, 1986

[54] SYNTHESIS OF MOLYBDENUM/ALKYLENE GLYCOL COMPLEXES USEFUL AS EPOXIDATION CATALYSTS

[75] Inventors: Edward T. Marquis, Austin; Kenneth P. Keating, Georgetown; John R. Sanderson; William A. Smith, both of Austin, all of Tex.

[73] Assignee: Texaco Inc., White Plains, N.Y.

[21] Appl. No.: 687,701

[22] Filed: Dec. 31, 1984

[51] Int. Cl.$^4$ .............................................. C07F 11/00
[52] U.S. Cl. ...................................................... 556/57
[58] Field of Search ....................... 260/429 R; 556/57

[56] References Cited

U.S. PATENT DOCUMENTS

| | | | |
|---|---|---|---|
| 2,795,552 | 6/1957 | Abbott et al. | 252/49.7 |
| 3,285,942 | 11/1966 | Price et al. | 260/429 |
| 3,350,422 | 10/1967 | Kollar | 260/348.5 |
| 3,351,635 | 11/1967 | Kollar | 260/348.5 |
| 3,362,972 | 1/1968 | Kollar | 260/414 |
| 3,434,975 | 3/1969 | Sheng et al. | 252/431 |
| 3,480,563 | 11/1969 | Bonetti et al. | 252/431 |
| 3,573,226 | 3/1971 | Sorgenti | 252/431 |
| 3,578,690 | 5/1971 | Becker | 260/414 |
| 3,666,777 | 5/1972 | Sorgenti | 260/348.5 |
| 3,668,227 | 6/1972 | Mattucci | 260/429 |
| 3,784,482 | 1/1974 | Cavitt | 252/431 |
| 3,787,329 | 1/1974 | Cavitt | 252/431 |
| 3,953,362 | 4/1976 | Lines et al. | 252/431 |
| 3,956,180 | 5/1976 | Cavitt | 252/431 |
| 3,991,090 | 11/1976 | Hagstrom et al. | 260/429 |
| 4,009,122 | 2/1977 | Lines et al. | 252/431 |

*Primary Examiner*—Helen M. S. Sneed
*Attorney, Agent, or Firm*—Jack H. Park; Kenneth R. Priem

[57] ABSTRACT

Complexes made by reacting an ammonium-containing molybdenum compound with an alkylene glycol in the presence of water at an elevated temperature are described. Mild stripping of the water subsequent to complex formation is preferred. If some of the water is left in the complex, it may serve as an excellent olefin epoxidation catalyst. The ratio of moles of alkylene glycol to gram atoms of molybdenum in the complex forming reaction ranges from 7:1 to 20:1. Ethylene glycol and propylene glycol are the particularly preferred alkylene glycols.

5 Claims, No Drawings

SYNTHESIS OF MOLYBDENUM/ALKYLENE GLYCOL COMPLEXES USEFUL AS EPOXIDATION CATALYSTS

CROSS-REFERENCE TO RELATED APPLICATION

This application is related to U.S. patent application Ser. No. 687,710, filed Dec. 31, 1984 which is concerned with the synthesis of molybdenum monohydric alcohol complexes also useful as molybdenum catalysts.

BACKGROUND OF THE INVENTION

1. Field of the Invention

The invention relates to the methods for making molybdenum compounds and more particularly relates to methods for making molybdenum alcohol complexes useful as olefin epoxidation catalysts.

2. Other Related Methods in the Field

It is well known that the epoxidation of olefins to give various oxide compounds has long been an area of study by those skilled in the art. It is equally well known that the reactivities of the various olefins differs with the number of substituents on the carbon atoms involved in the double bond. Ethylene itself has the lowest relative rate of epoxidation, with propylene and other alpha olefins being the next slowest. Compounds of the formula $R_2C=CR_2$, where R simply represents alkyl or other substituents, may be epoxidized fastest. Thus, the more substituents on the double bond carbons, the easier it is to epoxidize across that bond.

Of course, the production of ethylene oxide from ethylene has long been known to be accomplished by reaction with molecular oxygen over a silver catalyst. Numerous patents have issued on various silver-catalyzed processes for the production of ethylene oxide. Unfortunately, the silver catalyst route will not work for olefins other than ethylene. For a long time the commercial production of propylene oxide could only be accomplished via the cumbersome chlorohydrin process.

Another commercial process for the manufacture of substituted oxides from alpha olefins such as propylene was not discovered until John Kollar's work in the 1960s. His U.S. Pat. No. 3,351,635 taught that an organic oxide compound could be made by reacting an olefinically unsaturated compound with an organic hydroperoxide in the presence of a molybdenum, tungsten, titanium, columbium, tantalum, rhenium, selenium, chromium, zirconium, tellurium or uranium catalyst. Kollar's U.S. Pat. No. 3,350,422 teaches a similar process using a soluble vanadium catalyst.

However, even though Kollar's work was recognized as extremely important in the development of a commercial propylene oxide process that did not depend on the chlorohydrin route, it has been recognized that Kollar's catalytic route (in which molybdenum is the preferred catalyst) has a number of problems. For example, large quantities of the alcohol corresponding to the peroxide used were formed; if t-butyl hydroperoxide was used as a co-reactant, then a use or market for t-butyl alcohol had to be found. Other troublesome by-products were the olefin oligomers. If propylene was the olefin to be epoxidized, various propylene dimers, sometimes called hexenes, would result. Besides being undesirable in that the best use of propylene was not made, problems would be caused in separating the desired propylene oxide from the product mix. In addition, the molybdenum catalyst may not be stable or the recovery of the catalyst for recycle may be poor.

Various avenues of investigation have been explored in attempts to improve on the molybdenum-catalyzed epoxidation of propylene. One technique was to try to improve on the catalyst itself. Patents which cover the preparation of various molybdenum epoxidation catalysts include U.S. Pat. No. 3,362,972 to Kollar. There a hydrocarbon soluble salt of molybdenum or vanadium may be made by heating a molybdenum compound in which molybdenum has a valence of +6, or a vanadium compound in which vanadium has a valence of +5, with a carboxylic acid of from 4 to 50 carbon atoms having at least 4 carbon atoms per carboxylic group. U.S. Pat. No. 3,578,690 to Becker discloses that molybdenum acid salts may be made by directly reacting a carboxylic acid with a molybdenum compound while removing the water that is formed.

The reaction of molybdenum trioxide with monohydric saturated alcohols having 4 to 22 carbon atoms or with a mono- or polyalkylene glycol monoalkyl ether or mixtures thereof to make olefin epoxidation catalysts is described in U.S. Pat. No. 3,480,563 to Bonetti, et al. These catalysts have only 0.07 to 0.93% molybdenum, which is a molybdenum content too low for commercial use. Bonetti, et al. do not realize the importance of the ratio of alcohol to molybdenum compound reactants with respect to maximizing molybdenum content yet providing a soluble, active epoxidation catalyst. They also do not indicate any benefit from adding ammonium hydroxide to the preparation, an important factor discovered when molybdenum trioxide is reacted with 2-ethyl-1-hexanol.

In U.S. Pat. No. 3,434,975 to ARCO, investigators found that molybdenum catalysts could be made from saturated alcohols or glycols having one to four carbon atoms, such as ethylene glycol and propylene glycol, by reacting them with molybdenum metal and an organic hydroperoxide, peroxide, or $H_2O_2$. Molybdenum compounds prepared by reacting an ammonium-containing molybdate with a hydroxy compound, for example, an organic primary or secondary alcohol, a glycol or a phenol, are described in U.S. Pat. Nos. 3,784,482 and 3,787,329 to Cavitt.

Further, U.S. Pat. No. 3,573,226 to Sorgenti discloses that molybdenum-containing epoxidation catalyst solutions may be made by heating molybdenum powder with a stream containing unreacted tertiary butyl hydroperoxide and polyhydric compounds of from about 200 to 300 molecular weight and having from 4 to 6 hydroxyl groups per molecule. These catalysts are used for the epoxidation of propylene according to U.S. Pat. No. 3,666,777 to Sorgenti.

U.S. Pat. No. 3,953,362 to Lines, et al. reveals that novel molybdenum epoxidation catalysts may be prepared by reacting an oxygen-containing molybdenum compound with hydrogen peroxide and an amine and optionally water or an alkylene glycol at elevated temperatures. Similar catalysts are prepared by reacting an oxygen-containing molybdenum compound with an amine and an alkylene glycol at elevated temperatures according to U.S. Pat. No. 4,009,122 also to Lines, et al.

U.S. Patent to Mattucci, et al. also concerns molybdenum glycol catalysts prepared from molybdenum acetyl acetonate and isolated as solids. When the materials are used as epoxidation catalysts, they must be employed in solution with a hydrocarbon solvent. Molybdenum derivative compounds also useful as epoxidation catalysts may be prepared by reacting an oxygen-containing molybdenum compound such as molybdenum acetylacetonate, molybdic acids and molybdenum oxides with an organic compound having vicinal hydroxyl groups in the presence of a hydrohalic acid such as hydrofluoric acid, hydrochloric acid and the like, according to U.S. Pat. No. 3,991,090 to Hagstrom, et al.

There still exists a need for an epoxidation catalyst that is stable, easy to prepare, and has a high molybdenum content. Recent research also suggests that such a catalyst should also be nonacidic from the standpoint of not containing any excess or free carboxylic acid (solvent) if the catalyst involves reaction of molybdenum trioxide or ammonium heptamolybdate with a carboxylic acid.

SUMMARY OF THE INVENTION

The invention concerns molybdenum complexes made by reacting an ammonium-containing molybdenum compound with an alkylene glycol in the presence of water at an elevated temperature, and the use of these complexes as epoxidation catalysts.

DETAILED DESCRIPTION OF THE PREFERRED EMBODIMENTS

The improvements in the complexes of this invention relate to the discovery that the ratio of alkylene glycol reactant to molybdenum compound has an effect on the ease of filterability of the finished reaction mixture and the stability of the finished complex solution with respect to staying clear and solids-free over extended periods of time. Another improvement in the complex synthesis is related to the discovery that the actual molybdenum complex preparation history is very important in determining the final comlex is good or poor in its final application, such as an epoxidation catalyst. In the case of molybdenum complexes with EG (ethylene glycol) or PG (propylene glycol) used as epoxidation catalysts, the reaction temperature should not be too high (165° to 180° C.) as this results in low molybdenum contents in the complexes and the formation of large quantities of solids. Also, for complexes useful as epoxidation catalysts, the high molybdenum content must be achieved by adjusting the ratio of glycol to gram atoms of molybdenum, not by distilling off the glycol. If a lot of glycol is distilled to concentrate the molybdenum content of the complex, the water content of the complex will become too low and the complex will perform poorly as an epoxidation catalyst in that the selectivity based on the organic hydroperoxide consumed will be poor. The preferred procedure involves establishing the ratio of moles of glycol to gram atoms molybdenum in the 8:1 to 16:1 range which produces an essentially solids-free reaction mixture after digestion one hour at 90° to 120° C. Next, a vacuum stripping is conducted to remove water, ammonia, etc. so that the remaining bottoms are 80 to 95 wt.% of the charge.

The molybdenum compounds of this invention are preferably molybdenum compounds which contain ammonium ligands as well as oxygen. Such materials include ammonium heptamolybdate, ammonium dimolybdates, and hydrate forms thereof such as ammonium heptamolybdate tetrahydrate (the preferred method for having water present). Other ammonium heterpoly molybdates and mixtures thereof would also be useful. Molybdenum trioxide works to a degree, but not nearly as well as ammonium heptamolybdate or ammonium dimolybdate.

Alkylene glycols form the other class of co-reactants used to make the molybdenum complexes of this invention. These dihydric alcohols may be 1,2-diols; 1,3-diols or 1,4-diols. These alkylene glycols may also be represented by the structure $R\text{-CH(OH)-(CH}_2)_n\text{-CH(OH)-R}$ where R is hydrogen or an alkyl group of one to three carbon atoms and which may be joined to form a cyclohexane ring, and n is zero or two. The molecular weight of these glycols should be no more than about 200. Glycols which have been found to give high molybdenum content complexes, which are desired, include ethylene glycol, propylene glycol, 1,2-butane diol, 2,3-butane diol, 1,4-butane diol and 1,2-cyclohexane diol. Other diols, such as arylene diols, are no doubt also useful and this list is not meant to be exclusive. Diols such as 1,3-propane diol, 1,3-butane diol, 1,3-cyclohexane diol and 2,3-dimethyl-2,3-butane diol (pinacol) give complexes having low molybdenum contents which are undesirable. It is preferred that the alkylene glycol be ethylene glycol, propylene glycol or mixtures thereof.

Further, it has been found that not only the ratio of glycol (moles of glycol) to gram atoms of molybdenum compound and the temperature of complex preparation are important in determining the amount of molybdenum in the complex, the ease of processing and the storage stability of the complex with respect to the precipitation of solids, but also the nature of the molybdenum compound and the glycol are both important. For example, when molybdenum trioxide is used in place of ammonium heptamolybdate (AHM) or ammonium dimolybdate (ADM) in reaction with EG, the proportion of molybdenum in the complex was only 5.59% and the complex preparation took 18-20 hours. The complex also gave poor results as an epoxidation catalyst with respect to propylene oxide selectivity. The typical inventive EG and AHM or ADM complex preparation at about a 10:1 ratio gave molybdenum contents of from 10 to 20% depending on how much glycol was stripped. In another instance, complexes made using 1,3-diols were relatively poor epoxidation catalysts compared to those prepared from EG or PG.

For the alkylene glycol/molybdenum compound system, the preferred reactant ratios are 7:1 to 20:1 expressed in terms of moles of glycol to gram atoms of molybdenum in the ammonium-containing molybdenum compound. An especially preferred range of moles of glycol to gram atoms of molybdenum is 8:1 to 16:1. To provide the best complex in terms of molybdenum content, ease of processing and stability upon standing, the proportion of water remaining in the complex should be in the range of 0.5 to 6 wt.%. The reaction temperature to make the inventive complexes should be between about 80° and 130° C., preferably 90° to 120° C., and the pressure should be atmospheric. High reaction temperatures, on the order of 165° to 180° C. with molybdenum/EG or molybdenum/PG complex preparations lead to sharply reduced molybdenum contents, on the order of 2 to 3%, and large formation of solids. With the technique of this invention, liquid complexes with molybdenum contents of 6 to 24% are possible. Typically, these molybdenum contents are 10 to 20% or of the 12 to 16% narrower range which remains greater than that obtainable by prior methods. Such high levels of molybdenum in stable liquid complexes are much better than those attainable by the prior art and are definitely suitable for commercial use. Generally, no filtration is required for the best complexes of this invention. In a preferred embodiment, the reactants are heated to about 90° to 120° C. for about one hour, cooled a bit and then subjected to a vacuum of 10 to 100 mm Hg to remove water and glycol, for 30 to 60 minutes. The temperature of the pot should rise to about 90° to 110° C. during the stripping and the pressure should be adjusted to achieve and maintain this temperature. Sufficient overhead is removed so that the complex bottoms amount to about 80 to 95 wt.% of the charge and the water content of the catalyst is preferably in the 1 to 3 wt.% range. Generally, the water content of the final complex should be between about 0.5 and 6.0 wt.%, particularly for epoxidation purposes.

It should be noted that these complexes are surprisingly made very simply and require no corrosive acids, amines, etc. They are made at very mild temperatures and with short reaction times (about one hour as opposed to the 3-8 hours of other methods). The complexes require very little or no filtration and appear to remain stable indefinitely. In addition, the processing costs and reactant costs to make these complexes are minimal. For epoxidation purposes, the water content of the final complex should be between about 0.5 and 6 wt.%, and preferably between 1 and 3 wt.%.

The complexes and method of this invention are more particularly illustrated by the following examples which would not be construed as limiting the invention in any way.

Since the molybdenum/glycol complexes of this invention titrate as acids, even though they have no free acidic groups, their use as acid catalyst substitutes seems likely. For example, the instant complexes may be useful cyclization catalysts for splitting out water such as in the production of tetrahydrofuran from 1,4-butane diol and hydroxyethylpiperazine from triethylenediamine. The complexes of this invention might be used as catalysts for hydroxylations such as the production of resorcinol from toluene in the presence of a hydroperoxide, carbonate formations from olefins, carbon dioxide and a hydroperoxide, and oxygenate formations from hydrocarbons and organic hydroperoxides. Other catalytic uses for these complexes include condensations, dehydrations, esterifications, oligomerizations, polymerizations, disproportionations and rearrangements other than those mentioned. The molybdenum/glycol complexes could also be tried as corrosion inhibitors in antifreeze formulations and as direct additives to oils, greases and other lubricating fluids.

The examples herein also illustrate the use of the complexes of this invention as catalysts in epoxidation reactions, which have already been mentioned. Before addition, the complex-catalyst solution is usually premixed with one of the reactants, typically the hydroperoxide, such as a t-butyl alcohol (TBA) solution of t-butyl hydroperoxide (TBHP).

It is well known that soluble molybdenum complexes efficiently catalyze the epoxidation of propylene to propylene oxide in the presence of t-butyl hydroperoxide. However, the alkylene glycol/molybdenum complexes of this invention surprisingly give selectivities to propylene oxide in such reactions on the order of 98 to 99% and higher at TBHP conversions of about 98 to 98.4% while providing minimal propylene dimer production and very low methyl formate production.

The epoxidations are typically conducted by reacting an olefin with an organic hydroperoxide in the presence of a catalyst and a solvent. Preferably, the olefin is propylene and the hydroperoxide is TBHP. With these reactants, the desired product is propylene oxide (PO). As noted above, the catalyst is usually incorporated into one or the other of the reactants prior to introduction to the reactor.

Preferably, the catalyst concentration is from 200 to 600 ppm based on the combination of the olefin and the organic hydroperoxide. Further, the reaction should be conducted at a temperature in the range of 50° to 180° C., preferably 90° to 140° C. and especially in the range of about 100° to 130° C. This reaction temperature is relatively low as compared with other commercial techniques. Another unusual aspect is that the preferred mole ratio of olefin to hydroperoxide is unusually low; on the order of from about 0.9:1 to 3.0:1. All of these characteristics, together with the complexes of this invention as catalysts, provide an epoxidation process which gives excellent results.

Specifically, it was found that these very high molybdenum concentration alkylene glycol complexes are far better in propylene epoxidations, using organic hydroperoxides such as TBHP, than corresponding complexes with low molybdenum concentrations, provided that the complexes of this invention are made to be concentrated in molybdenum by using a low alcohol to gram atom of molybdenum mole ratio, such as 8:1 to 15:1 as opposed to making the complex dilute (for example, at ratios of 20:1 to 50:1), then concentrating it by distilling off glycol. The high molybdenum concentration complexes made by the latter technique are very poor epoxidation catalysts. The differences in result hold true even when the amount of molybdenum in ppm based on the total reactor charge is similar. Again, the best results in the epoxidation reactions are obtained when lightly stripped materials are used, rather than complexes that have all of the water present or have all of the water removed.

Another preferred embodiment of the epoxidations involves conducting the reaction in two stages, approximately equal in length, with the first stage at a lower temperature than the second stage. For instance, the first hour of reaction would preferably be conducted at a temperature in the range of 50° to 120° C. followed by the second and last hour of reaction at about 120° to 150° C.

Complexes with 17 to 24 wt.% molybdenum contents were prepared at about 6:1 to 10:1 moles of glycol to gram atoms of molybdenum ratios and more severe stripping conditions, but these complexes generally tended to precipitate crystals which did not easily redissolve upon heating. Further, the EG or PG complexes which were excessively stripped tended to have very low water contents and performed poorly in epoxidations. Dilute molybdenum/EG or PG complexes having 2.5 wt.% molybdenum also did not give good results as epoxidation catalysts. Again, best results are obtained in the epoxidations if the complexes have 12 to 16 wt.% molybdenum contents, made at the appropriate ratios and temperatures with the mild stripping procedures described above.

A 12 to 16 wt.% molybdenum complex which performed well as an epoxidation catalyst, when subsequently diluted with EG or PG performed poorly in epoxidations after dilution. Likewise, dilute molybdenum catalyst (1 to 2 wt.% molybdenum) that were concentrated by stripping to 10 and 20% molybdenum also gave poor results in epoxidations. Adding water back to these stripped, concentrated catalysts with heating did not restore their previous ability to give only acceptable selectivities to the desired epoxidation catalysts. In summary, the precise nature of the complexes of this invention is critical to obtaining excellent results when they are used as epoxidation catalysts. When properly made, these complexes require no filtration and remain stable upon standing for months.

If the water is left in these complexes and they are not stripped, the selectivities which they give when used as epoxidation catalysts remain excellent, but two problems result. One, solids form when the catalyst is mixed with the hydroperoxide/alcohol reactant solution, and two, the complex is relatively unstable and may precipitate solids at any time. Therefore, vacuum stripping is highly preferred.

It is very surprising that essentially quantitative selectivities and conversions can be obtained with these molybdenum/alkylene glycol catalysts. The substantial body of existing literature (journals and patents) suggests that all soluble molybdenum catalysts will perform about the same with only small differences because in the epoxidation all catalysts are allegedly converted to glycol-like catalysts. It is thus surprising that the results using the complexes of this invention as epoxidation catalysts are so clearly superior to any catalysts taught in the literature. It is further surprisingly that these high molybdenum complexes work so much better than more dilute catalysts although equal ppm molybdenum are present in the reaction, and that complexes with limited amount of water in them work so well as catalysts.

CATALYST PREPARATIONS

EXAMPLE 1

This example will illustrate the typical preparation of these molybdenum/alkylene glycol complexes. Since water is employed (in the hydrate) a complex with excellent epoxidation properties was produced.

To a one-liter round-bottomed Morton flask was added 80.0 g of ammonium heptamolybdate tetrahydrate and 300.0 g of propylene glycol. The reaction mixture was heated to 90°–100° C. for 1.0 hours with nitrogen slowly passing through the flask, fitted with a mechanical stirrer, nitrogen inlet, thermometer, Dean Stark trap, condenser, and nitrogen bubbler. After the reaction was over, essentially all of the AHM was dissolved and the reaction mixture was cooled and subjected to an aspirator vacuum and the mixture reheated to 90°–100° C. for about 1 to 2 hours. The catalst was a clear yellowy color containing 13.9% molybdenum by Atomic Absorption spectroscopy and 2.70% water (Karl Fisher analysis) and 0.87% nitrogen (Kjeldahl). Further, the catalyst titrated as having two strongly acidic protons exhibiting acid breaks at 63.8 mg KOH/g of sample and 136.97 mg KOH/g of sample.

EXAMPLE 2

A complex prepared as follows with no water present had very poor epoxidation characteristics, especially giving a poor selectivity to propylene oxide. The selectivity to propylene oxide in a comparable epoxidation using the complex of Example 1 gave a 97.7% selectivity to propylene oxide. The catalyst was made in a similar fashion to Example 1 except that 500 g PG was slowly reacted with 80.0 g AHM and after reaction, some 200 g PG was slowly distilled off at pump vacuum (less than 5 mm) and about 100° C. The finished catalyst had only 0.06% water remaining and 14.9% moly content.

EXAMPLES 3–12

Catalyst preparation Examples 3 through 12 are summarized in Table I. These experiments were performed using the procedures of Example 1 except for the changes noted.

TABLE I

PROPYLENE GLYCOL/MOLYBDENUM COMPLEXES

| Example | Propylene Glycol Grams | Propylene Glycol Moles | AHM[a] Grams | Mo, Gram Atoms | Mole Ratio PG/g Atoms Mo | Catalyst Preparation Temp. °C. | Time of Run (hr.) | Stripping Temp. (°C.) | Stripping Time (hr.) | % Mo | % $N_2$ | % $H_2O$ | Acid # mg. KOH g sample |
|---|---|---|---|---|---|---|---|---|---|---|---|---|---|
| 3[b] | 100.0 | 1.316 | c | 0.0136 | 96.76/1 | 93–100 | 0.67 | 100 | 0.16 | 1.07 | ND[d] | 0.48 | ND |
| 4[b] | 100.0 | 1.316 | 2.0[e] | 0.0136 | 96.76/1 | 161–162 | 3.0 | 113 | 0.16 | 1.29 | ND | 0.24 | 8.29 |
| 5 | 100.0 | 1.316 | 10.0[e] | 0.0678 | 19.41/1 | 129–130 | 2.0 | None | — | 6.19 | ND | 1.30 | 27.22 53.43 |
| 6 | 100.0 | 1.316 | 20.0[e] | 0.1357 | 9.70/1 | 130–132 | 2.5 | None | — | 9.46 | ND | 4.14 | 48.71 91.51 |
| 7[b] | 300.0 | 3.947 | 60.0[f] | 0.3398 | 11.615/1 | 100–104 | 2.0 | 80–90[g] | 1.0 | 10.3 | 0.64 | 2.47 | 50.84 109.21 |
| 8 | (0.52 g of catalyst from Ex. 7 plus 35.5 g propylene glycol) | | | | | | | | | 1.281 | — | 0.31 | — |
| 9[h] | 500.00 | 6.579 | 80.0[f] | 0.4531 | 14.52/1 | 100 | 1.16 | 97–100 | 0.75 | 14.9 | 0.42 | 0.06 | 18.99 68.24 141.75 |
| 10[b] | 300.0 | 3.947 | 80.0[f] | 0.4531 | 8.711/1 | 95–97 | 1.0 | 90 | 1–2 | 13.9 | 0.87 | 2.70 | 63.80 136.97 |
| 11 | (added 1.0 g $H_2O$ to 50 g of Ex. 9, 1.96% $H_2O$, and heat to 100° C. for one hour) | | | | | | | | | 14.6[i] | — | 1.96 | — |
| 12 | (added 2.0 g $H_2O$ to 50 g of Ex. 9, 3.8% $H_2O$, and heat to 100° C. for one hour) | | | | | | | | | | | | |

[a]AHM is ammonium heptamolybdate
[b]Aspirator used for vacuum
[c]2.0 g of $MoO_3$ used with 1.0 m. $NH_4OH$
[d]ND means not determined
[e]Baker's ammonium molybdate hydrate used, analyzed as 65.1% Mo
[f]Climax AHM $4H_2O$ used, analyzed as 54.34% Mo
[g]Buchii Stripping used
[h]High vacuum pump used for vacuum
[i]Calculated values

EXAMPLES 13–22

The epoxidations shown in Table II were done in a 300 ml stainless steel autoclave by charging propylene first at ambient temperature, then charging the hydroperoxide (in this case, t-butyl hydroperoxide or TBHP)

premixed with molybdenum-PG (propylene glycol) catalyst all at once also at ambient temperature. The reaction mixture was heated to 110° C. for one hour then heated further to 130°-140° C. where the reaction mixture was held for another hour. The reaction mixture was cooled and sampled under pressure and analyzed by GLC for wt.% propylene oxide (PO). The reaction mixture was also sampled a second time under pressure and this sample distilled to remove propylene. The liquid sample was analyzed for TBHP remaining and ppm metals. By ratioing the liquid remaining after propylene removal to the charge to the distillation and comparing this ratio with the total product, the amount of total liquid minus propylene, was obtained, and from this weight and TBHP analysis the amount of TBHP remaining was determined. Subtracting this from the amount of TBHP fed gave the amount of TBHP reacted. From these values the conversion of TBHP, selectivity of PO based on TBHP consumed and yield of PO based on TBHP charged were calculated.

In runs 13, 14, 15, 16 and 17 (Table II) we see the effect of increasing molybdenum concentration in the catalyst. Runs 13 and 14 with low molybdenum concentration provide 76 and 79% PO selectivity, whereas runs 6 and 17 with 9.46% and 10.3% molybdenum provide 95.3 and 95.7% PO selectivity. Further, the concentration effect is dramatically illustrated by looking at runs 17 and 18 using the same catalyst as run 17, but diluted with the solvent used in all the catalyst preparations, propylene glycol. In run 18 the catalyst was diluted to 1.28% molybdenum with propylene glycol and the selectivity dropped from 95.7% to 78.8%. Run 20 illustrates another high molybdenum concentration run affording excellent selectivity (97.7%).

The effect of molybdenum concentration has been amply discussed, now for the equally dramatic effect of water concentration. In run 19, a high molybdenum concentration catalyst was prepared in which the water level was reduced to 0.06% water by low temperature codistillation of propylene glycol and water under high vacuum. In run 19 the selectivity was lowered from the 95-97% range (runs 17 and 20) to 88.2% and the make of propylene dimer went up 10- to 12-fold from 20 to 38 to 385 ppm. Attempting to add water back to the dry catalyst runs 21 and 22 did help the propylene dimer make, lowering it from 385 to 243 (1.96% water added) and to 105 ppm (3.8% water added) but the selectivity still only came up to 89.5% in run 22 from the 88.2% observed in run 19 and still far below the selectivities observed in run 17 (95.7% with 2.47% water in the catalyst), run 16 (95.4% with 14.4% water in the catalyst) and run 20 (97.7% with 2.70% water in the catalyst).

In order to prepare the most active and selective molybdenum-propylene glycol catalysts, the mole ratio of alcohol to gram atoms molybdenum should be in the range of 7:1 to 20:1, preferably 8:1 to 12:1 and the source of the molybdenum should be ammonium heptamolybdate (tetrahydrate). The catalysts are best prepared by heating propylene glycol and ammonium heptamolybdate at 80°-130° C. (preferably 90°-100° C.) for 1 to 2 hours under nitrogen with vigorous stirring. The reaction mixture should then be cooled and subjected to aspirator vacuum and water removed at temperatures not exceeding 90° to 100° C. until the catalyst has a water content of about 0.5 to 0.6% water) preferably 2 to 5% water).

TABLE II

EPOXIDATIONS USING MOLYBDENUM/PROPYLENE GLYCOL COMPLEXES AS CATALYSTS

| Ex. | Temp. (C.) | Time (Hr.) | Mo Catalyst Conc. | Catalyst From Ex. | Molar Ratio C3:HP | HP:TBA | PO Conc. | Yield | Selectivity of TBHP to PO | Prop. to PO |
|---|---|---|---|---|---|---|---|---|---|---|
| 13 | 110 | 1.0 | .0245 | 3 | 1.20 | 2.14 | 24.07 | 74.51 | 76.44 | 85.03 |
|  | 140 | 1.0 |  |  |  |  |  |  |  |  |
| 14 | 110 | 1.0 | .0246 | 4 | 1.22 | 2.14 | 25.21 | 78.01 | 79.26 | 87.41 |
|  | 140 | 1.0 |  |  |  |  |  |  |  |  |
| 15 | 110 | 1.0 | .0250 | 5 | 1.18 | 2.14 | 29.00 | 87.56 | 89.00 | 90.95 |
|  | 140 | 1.0 |  |  |  |  |  |  |  |  |
| 16 | 110 | 1.0 | .0253 | 6 | 1.17 | 2.14 | 30.84 | 92.85 | 95.35 | 98.11 |
|  | 140 | 1.0 |  |  |  |  |  |  |  |  |
| 17 | 110 | 1.0 | .0300 | 7 | 1.18 | 2.14 | 30.32 | 91.55 | 95.70 | 97.47 |
|  | 130 | 1.0 |  |  |  |  |  |  |  |  |
| 18 | 110 | 1.0 | .0294 | 8 | 1.16 | 2.14 | 23.75 | 72.73 | 78.77 | 88.06 |
|  | 130 | 1.0 |  |  |  |  |  |  |  |  |
| 19 | 110 | 1.0 | .0349 | 9 | 1.19 | 2.14 | 28.93 | 87.48 | 88.20 | 89.42 |
|  | 135 | 1.0 |  |  |  |  |  |  |  |  |
| 20 | 110 | 1.0 | .0318 | 10 | 1.19 | 2.14 | 31.32 | 94.55 | 97.70 | 96.65 |
|  | 135 | 1.0 |  |  |  |  |  |  |  |  |
| 21 | 110 | 1.0 | .0352 | 11 | 1.15 | 2.14 | 28.58 | 85.55 | 87.11 | 89.95 |
|  | 135 | 1.0 |  |  |  |  |  |  |  |  |
| 22 | 110 | 1.0 | .0357 | 12 | 1.12 | 2.14 | 29.29 | 86.98 | 89.49 | 92.18 |
|  | 135 | 1.0 |  |  |  |  |  |  |  |  |

| Ex. | Temp. (C.) | Time (Hr.) | TBHP Conv. | Prop. Conv. | Balances C | O | Moly | Mo Conc. PPM | Dimer ppm Pure PO Basis | TBHP Wt. % Remain in Liq. |
|---|---|---|---|---|---|---|---|---|---|---|
| 13 | 110 | 1.0 | 97.47 | 72.81 | 99.3 | 95.3 | 252 | 750 | 129 | 1.54 |
|  | 140 | 1.0 |  |  |  |  |  |  |  |  |
| 14 | 110 | 1.0 | 98.43 | 73.26 | 98.9 | 94.9 | 171 | 506 | 226 | 0.95 |
|  | 140 | 1.0 |  |  |  |  |  |  |  |  |
| 15 | 110 | 1.0 | 98.39 | 81.56 | 99.3 | 97.6 | 89 | 267 | 134 | 1.00 |
|  | 140 | 1.0 |  |  |  |  |  |  |  |  |
| 16 | 110 | 1.0 | 97.38 | 80.63 | 99.8 | 99.1 | 91 | 277 | 20 | 1.63 |

TABLE II-continued
EPOXIDATIONS USING MOLYBDENUM/PROPYLENE GLYCOL COMPLEXES AS CATALYSTS

| | | | | | | | | | |
|---|---|---|---|---|---|---|---|---|---|
| 17 | 140 | 1.0 | 95.66 | 79.30 | 99.7 | 99.5 | 100 | 362 | 21 | 2.69 |
| | 110 | 1.0 | | | | | | | | |
| | 130 | 1.0 | | | | | | | | |
| 18 | 110 | 1.0 | 92.34 | 71.30 | 99.6 | 95.6 | 103 | 364 | 40 | 4.66 |
| | 130 | 1.0 | | | | | | | | |
| 19 | 110 | 1.0 | 99.19 | 82.04 | 97.5 | 96.4 | 71 | 297 | 385 | 0.50 |
| | 135 | 1.0 | | | | | | | | |
| 20 | 110 | 1.0 | 96.78 | 82.51 | 99.4 | 99.2 | 81 | 299 | 38 | 1.93 |
| | 135 | 1.0 | | | | | | | | |
| 21 | 110 | 1.0 | 98.20 | 82.50 | 98.2 | 96.5 | 86 | 346 | 243 | 1.07 |
| | 135 | 1.0 | | | | | | | | |
| 22 | 110 | 1.0 | 97.20 | 84.45 | 98.6 | 96.4 | 90 | 371 | 105 | 1.69 |
| | 135 | 1.0 | | | | | | | | |

EXAMPLES 23-27

Examples 23 through 27 were conducted according to the procedure of Example 1 with the changes as noted in Table III with the additional change that the alkylene glycol used throughout was ethylene glycol (EG) instead of propylene glycol (PG).

formate contents for the products of these experiments is also given.

Examples 30-33 illustrate the superior selectivity achieved when the molybdenum-ethylene glycol complexes are used as catalysts: selectivities to propylene oxide range from 98.3 to 99.4%. The hydroperoxide conversions were also excellent, ranging from 96 to

TABLE III
ETHYLENE GLYCOL/MOLYBDENUM COMPLEXES

| Run No. | Ethylene Glycol Grams | Moles EG | AHM, g | Mo in AHM, g | Mole Ratio EG/g Atoms Mo | Catalyst Preparation Temp., °C. | Time of Reaction (Hr.) | Stripping Temp., °C. | Stripping Time, hr. | % Mo | % $N_2$ | % $H_2O$ | Acid No. mg KOH g Sample |
|---|---|---|---|---|---|---|---|---|---|---|---|---|---|
| 23[a] | 100.0 | 1.613 | 2.0[b] | 0.0136 | 118.8:1 | 110 | 0 | 110 | 0.16 | 1.17 | ND | ND | ND |
| 24[a] | 100.0 | 1.613 | [c] | 0.136 | 118.8:1 | 110 | 0 | 100 | 0.33 | 1.10 | ND | ND | ND |
| 25[d] | 300.0 | 4.839 | 100.0 | 0.5664 | 8.543:1 | 85-110 | 1.0 | 90-95 | 1.5 | 16.1 | 1.17 | 1.67 | 80.94 167.85 |
| 26[a] | 375.0 | 6.048 | 100.0 | 0.5664 | 10.68:1 | 97-100 | 1.0 | 85-95 | 1-2[e] | 11.0 | 1.04 | 3.33 | 61.21 129.06 |
| 27[f] | 375.0 | 6.048 | 100.0 | 0.5664 | 10.68:1 | 97-100 | 1.0 | 91-93 | 0.16 | 15.5 | 0.87 | 1.58 | 86.92 183.88 |

[a]Aspirator used for vacuum
[b]Baker's ammonium molybdate hydrate used, analyzed as 65.1% Mo
[c]2.0 g $MoO_3$ and 1 ml $NH_4OH$ used
[d]Aspirator used 1 hour; high vacuum pump used 0.5 hr.
[e]Buchii stripping used
[f]High vacuum pump used for vacuum

EXAMPLES 28-33

Epoxidation Examples 28 through 33 demonstrate how the complexes made in Examples 23 through 27 may be used as catalysts for the epoxidation of propylene to propylene oxide. The procedure used for these epoxidations was the same as that used for Examples 13 through 22 except as noted in Table IV. The methyl 98.4%. In addition, the undesired propylene dimer by-product make is minimal, as low as 13 ppm based on the pure propylene oxide content (after unreacted propylene is removed). Although methyl formate by-product production was up for Examples 30-33 as compared with Example 28 and 29, these are not troublesome levels.

TABLE IV
EPOXIDATIONS USING MOLYBDENUM/PROPYLENE GLYCOL COMPLEXES AS CATALYSTS

| Ex. | Temp. (C.) | Time (Hr.) | Mo Catalyst Conc. | Catalyst From Ex. | Molar Ratio C3:HP | Molar Ratio HP:TBA | PO Conc. | Yield | Selectivity of TBHP to PO | Selectivity of Prop. to PO |
|---|---|---|---|---|---|---|---|---|---|---|
| 28[f] | 110 | 1.0 | .0195 | 23 | 3.06 | 1.26[g] | 18.75 | 82.81 | 94.92 | 88.57 |
| 29[e] | 110 | 1.0 | .0341 | 24 | 2.97 | 1.28[h] | 17.85 | 82.92 | 93.13 | 99.01 |
| 30[c] | 110 | 1.0 | .0391 | 25 | 1.18 | 2.14 | 31.77 | 95.81 | 99.09 | 97.37 |
| | 135 | 1.0 | | | | | | | | |
| 31[d] | 110 | 1.0 | .0253 | 26 | 1.19 | 2.14 | 31.98 | 96.70 | 98.30 | 100.09 |
| | 135 | 1.0 | | | | | | | | |
| 32[b] | 110 | 1.0 | .0350 | 26 | 1.15 | 2.14 | 32.00 | 95.78 | 99.39 | 99.84 |
| | 125 | 1.0 | | | | | | | | |
| 33[a] | 110 | 1.0 | — | 27 | 1.16 | 2.15 | 31.64 | 94.45 | 98.45 | 98.75 |
| | 125 | 1.0 | | | | | | | | |

| Ex. | Temp. (C.) | Time (Hr.) | TBHP Conv. | Prop. Conv. | Balances C | Balances O | Balances Moly | Mo Conc. PPM | ppm Pure PO Basis | TBHP Wt. % Remain in Liq. |
|---|---|---|---|---|---|---|---|---|---|---|
| 28[f] | 110 | 1.0 | 87.23 | 36.50 | 94.3 | 88.8 | 88.8 | 293 | ND | — |

TABLE IV-continued
EPOXIDATIONS USING MOLYBDENUM/PROPYLENE GLYCOL COMPLEXES AS CATALYSTS

| | | | | | | | | | | |
|---|---|---|---|---|---|---|---|---|---|---|
| 29[e] | 110 | 1.0 | 89.04 | 30.41 | 99.3 | 92.0 | 87.7 | 329 | ND | — |
| 30[c] | 110 | 1.0 | 96.69 | 83.20 | 99.7 | 99.9 | 92.6 | 380 | 16 | 2.05 |
| | 135 | 1.0 | | | | | | | | |
| 31[d] | 110 | 1.0 | 98.37 | 81.22 | 100.0 | 98.6 | 111.0 | 463 | 47 | 1.01 |
| | 135 | 1.0 | | | | | | | | |
| 32[b] | 110 | 1.0 | 96.37 | 83.63 | 100.3 | 99.3 | 125.8 | 510 | 13 | 2.18 |
| | 125 | 1.0 | | | | | | | | |
| 33[a] | 110 | 1.0 | 96.44 | 82.76 | 100.0 | 99.1 | 115.6 | 459 | 18 | 2.08 |
| | 125 | 1.0 | | | | | | | | |

[a]Methyl formate content was 0.029% when PO was 31.642%
[b]Methyl formate content was 0.030% when PO was 32.00%
[c]Methyl formate content was 0.035% when PO was 31.77%
[d]Methyl formate content was 0.054% when PO was 31.98%
[e]Methyl formate content was 0.190% when PO was 17.85%
[f]Methyl formate content was 0.214% when PO was 18.57%
[g]60.5% TBHP
[h]60.7% TBHP Many modifications may be made by one skilled in the art in this invention without changing the spirit and scope thereof which are defined only in the appended claims. The catalysts of this invention have a high molybdenum content, are stable upon standing and are easily filterable, and provide better epoxidation results in terms of selectivity to propylene oxide and low propylene dimer make and high propylene oxide concentrations than any catalysts mentioned in the journal or patent literature, especially at the low propylene to TBHP ratios examined.

We claim:

1. A method for preparing a catalytically active molybdenum complex which comprises:
   a. reacting at an elevated temperature between about 80° and 130° C. a reaction mixture consisting essentially of an undiluted ammonium-containing molybdenum compound with an undiluted alkylene glycol such that the ratio of moles of alkylene glycol to gram atoms of molybdenum ranges from about 7:1 to 20:1, in the presence of a minor amount of water, and
   b. subsequently mildly stripping the product from step a. to give said catalytically active molybdenum complex, said molybdenum complex having a final water content of about 0.5 to 6 wt.%.
   said alkylene glycol having a molecular weight of less than about 200 and containing only primary or secondary hydroxyl groups, said hydroxyl groups being separated from each other by an even number of carbon atoms.

2. A method of preparing a catalytically active molybdenum/alkylene glycol complex which comprises reacting a reaction mixture consisting essentially of an undiluted hydrate of an ammonium-containing molybdenum compound at atmospheric pressure at a temperature of about 80° to about 130° C. for about 1 to 2 hours with from about 7 to 20 moles per gram atom of molybdenum of an undiluted alkylene glycol, and then vacuum stripping the reaction product at a temperature of about 90° to about 110° C. to remove volatile by-products of the reaction, including water, to provide, as said catalytically active molybdenum/alkylene glycol complex, a stripped reaction product constituting about 80 to about 95 wt.% of the charge and having a molybdenum content of about 6 wt.% to about 20 wt.% and a water concentration of about 0.5 wt.% to about 6 wt.%, said alkylene glycol having a molecular weight of less than 200 and containing only primary or secondary hydroxyl groups, said hydroxyl groups being separated from each other by an even number of carbon atoms.

3. A method of preparing a catalytically active molybdenum/alkylene glycol complex which comprises the steps of:
   preparing a reaction mixture consisting essentially of an undiluted ammonium heptamolybdate tetrahydrate or ammonium dimolybdate hydrate and about 7 to 20 moles per gram atom of molybdenum of undiluted ethylene glycol or propylene glycol and heating said reaction mixture at atmospheric pressure to a temperature within the range of about 80° to about 130° C. for a reaction time of about 1 to 2 hours to provide a reaction product,
   cooling said reaction product and then vacuum stripping said reaction product at a temperature of about 90° about 110° C. for about 1 to about 2 hours sufficient to remove volatile by-products of the reaction, including water, by an amount sufficient to provide said catalytically active molybdenum/glycol complex constituting about 80 to about 95 wt.% of the reaction mixture and having a molybdenum content of about 6 wt.% to about 20 wt.% and a water concentration of about 0.5 wt.% to about 6 wt.%.

4. A method as in claim 3 wherein the reaction mixture consists essentially of ammonium heptamolybdate tetrahydrate and ethylene glycol.

5. A method as in claim 3 wherein the reaction mixture consists essentially of ammonium heptamolybdate tetrahydrate and propylene glycol.

* * * * *